United States Patent [19]
Chapman

[11] Patent Number: 4,730,077
[45] Date of Patent: Mar. 8, 1988

[54] METHOD OF PREPARING α-ARYLALKANOIC ESTERS

[75] Inventor: Robert C. Chapman, Manchester, Mo.

[73] Assignee: Mallinckrodt, Inc., St. Louis, Mo.

[21] Appl. No.: 888,538

[22] Filed: Jul. 12, 1986

[51] Int. Cl.$^4$ ............................................. C07C 69/76
[52] U.S. Cl. ..................................... 560/105; 560/19; 560/55
[58] Field of Search ........................... 560/105, 19, 55

[56] References Cited

U.S. PATENT DOCUMENTS 4,316,046  2/1982  Costa .................................. 560/105

FOREIGN PATENT DOCUMENTS 8021644    2/1983  Japan ................................. 560/105
59-163345  9/1984  Japan .

OTHER PUBLICATIONS

Tamura et al., *Synthesis*, pp. 231–232 (Mar. 1984).
A Goosen and C. W. McCleland, *J. Chem. Soc., Chem. Commun.*, pp. 1311–1312 (1982).
Y. Hamada and T. Shioiri, *Tetrahedron Lett.*, 23(2), pp. 235–236 (1982).
S. D. Higgins and C. B. Thomas, *J. Chem. Soc., Perkin Trans. I*, pp. 235–242 (1982).
K. Fujii et al., *Synjthesis*, pp. 456–457 (1982).
B. Myrboh et al., *Synthesis*, pp. 126–127 (1981).
G. Tsuchihashi et al., *Tetrahedron Lett.*, 22(43), pp. 4305–4308 (1981).
T. Shioiri and N. Kawai, *J. Org. Chem.*, 43(14), pp. 2936–2938 (1978).
A. McKillop et al., *J. Am. Chem. Soc.*, 95(10), pp. 3340–3343 (1973).
J. G. Sharefkin et al., *Organic Syntheses*, Coll. vol. 5, pp. 660–663 (1973).

*Primary Examiner*—Paul J. Killos
*Attorney, Agent, or Firm*—R. J. Klostermann; L. N. Goodwin; Veo Peoples

[57] ABSTRACT

Alpha-arylalkanoic esters are prepared by reacting a trivalent iodine compound of the formula

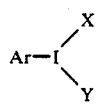

wherein Ar is an aromatic hydrocarbon and X and Y each represents a group which can be removed as an anion, with a carbonyl compound of the formula

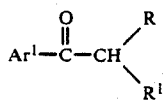

where $Ar^1$ is an aromatic hydrocarbon, R is a hydrogen atom or an alkyl group, and $R^1$ is a hydrogen atom or an alkyl group, in the presence of an orthocarboxylic ester having the general formula $ZC(OR^2)_3$, wherein $R^2$ is an alkyl group and Z is a hydrogen atom or an alkyl group; the reaction being carried out in a substantially anhydrous reaction mixture.

25 Claims, No Drawings

METHOD OF PREPARING α-ARYLALKANOIC ESTERS

TECHNICAL FIELD

The present invention relates to a method of preparing α-arylalkanoic esters.

BACKGROUND OF THE INVENTION

Alpha-arylalkanoic acids are widely used as active anti-inflammatory, analgesic, and anti-pyretic pharmaceutical products. Such acids include, for example, ibuprofen, 2-(4-isobutylphenyl)propionic acid and fenoprofen, 2-(3-phenoxyphenyl)propionic acid. Various methods are known in the art for making these acids and their corresponding esters. For example, α-arylalkanoic esters can be made from corresponding carbonyl compounds of the general formula:

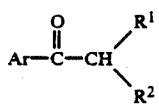

wherein at least one of the $R^1$ and $R^2$ groups is an alkyl group and the other is a hydrogen atom or an alkyl group or wherein $R^1$ is a bromine atom and $R^2$ is an alkyl group (*Journal Am. Chem. Soc.*, 95:3340 [1973]; *Synthesis*, p. 126, [1981]; *Synthesis*, p. 456, [1982]; *Parkin Transactions* (British Chem. Soc.), 1:235 [1982]; *Tetrahedron Letters*, 23:235 [1982], *Tetrahedron Letters* 22:4305 [1981]; *Journal Organic Chemistry*, 43:2936 [1978]; *Chemical Communications*, p. 1311, [1982].

Each of the aforementioned methods has at least one disadvantage, such as requiring the use of a poisonous thallium or lead salt or a precious, and expensive, silver salt, requiring a lengthy reaction time, and producing the desired product in low yields. Y. Tamura, Japanese Patent Publication No. Sho 59 [1984]-163,345, laid open Sept. 14, 1984, discloses a method of preparing α-arylalkanoic esters represented by the general formula

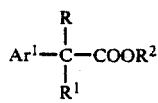

wherein $Ar^1$ is an aromatic hydrocarbon group, R and $R^1$ each represent a hydrogen atom or an alkyl group, and $R^2$ is an alkyl group, by reacting a compound of trivalent iodine having the general formula

wherein Ar is an aromatic hydrocarbon group and X and Y are each a group which can be eliminated as an anion, with a carbonyl compound having the general formula

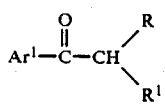

wherein $Ar^1$, R, and $R^1$ are as defined above. As disclosed therein, the reaction is effected in the presence of an orthocarboxylic ester having the general formula $ZC(OR^2)_3$, wherein $R^2$ is an alkyl group and Z is a hydrogen atom or an alkyl group. According to the Tamura disclosure, the reaction can be completed smoothly within a short period of time via heating in the presence of concentrated sulfuric acid. Example 1 thereof discloses heating and agitating 1 mmole of p-isobutylpropiophenone and 1 mmol of iodobenzene diacetate in 1.5 ml (13.7 mmol) o-formic acid methyl ester in the presence of 1 mmole concentrated sulfuric acid for 30 minutes to obtain ibupurophene [sic] methyl ester. Similarly, synthesis of methyl 2-arylpropanoates (such as the methyl ester of ibuprofen) from aryl ethyl ketones (such as p-isobutylphenyl ethyl ketone, i.e. p-isobutylpropiophenone) using diacetoxyphenyliodine (also known as iodobenzene diacetate) wherein the reaction is performed in trimethyl orthoformate in the presence of sulfuric acid (10 mmol per 5 mmol of ketone in typical procedure) is disclosed by Tamura et al., *Synthesis*, March 1984, 231–232. Although the method of Tamura (and co-workers) appears to eliminate one or more disadvantages of methods disclosed in the older art, it neither recognizes nor overcomes the problems resulting from attempting to conduct the reaction in the presence of water, such as reduced yields of the arylalkanoic esters. Trivalent iodine compounds within the above formula, e.g. iodobenzene diacetate, are typically contaminated with water in amounts up to 10% as a result of their preparation in aqueous systems. Moreover, although such compounds may be dried via vacuum dessication (Sharefkin et al., *Organic Syntheses*, Coll. Vol. 5, 660–663 [1973] or oven drying, such methods are slow and tedious, while oven drying presents risks of explosion and loss of the iodine compound. Accordingly, there is a substantial need in the art for improvements in the above-described Tamura method, whereby the above-noted problems are at least substantially diminished.

The present invention recognizes the above-noted problems and fulfills the above need by providing a low-cost improvement in the Tamura method, wherein water-containing trivalent iodine compounds are chemically dried with anhydrides in the presence of the carbonyl compound or ketone, with essentially no loss in yield as would result from reaction of the anhydride with the ketone or the iodine compound and/or interraction between the ketone and the iodine compound.

DESCRIPTION OF THE INVENTION

In accordance with the present invention, α-arylalkanoic esters of the general formula

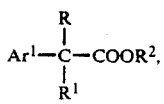

wherein $Ar^1$ is an aromatic hydrocarbon group, R and $R^1$ are each a hydrogen atom or an alkyl group, and $R^2$ is an alkyl group, are prepared by reacting a compound of trivalent iodine having the general formula

wherein Ar is an aromatic hydrocarbon group and X and Y are each a group which can be eliminated as an anion, with a carbonyl compound having the general formula

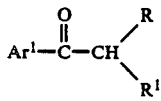

wherein $Ar^1$, R, and $R^1$ are as defined above, in the presence of an orthocarboxylic ester having the general formula $ZC(OR^2)_3$, wherein $R^2$ is an alkyl group and Z is a hydrogen atom or an alkyl group, via an improved method wherein the reaction is effected in a substantially anhydrous reaction mixture, preferably prepared by a process wherein said trivalent iodine compound is provided as a substance comprising water, which comprises contacting a carboxylic anyhydride with said substance in the presense of said carbonyl compound under conditions effective for converting at least a sufficient portion of the water to the acid corresponding to said anhydride to provide at least a portion of said reaction mixture. Preferably, such contacting is effected in the additional presence of sulfuric acid in a catalytically effective amount.

DETAILED DESCRIPTION OF THE INVENTION AND OF THE MANNER AND PROCESS OF MAKING AND USING IT

The present invention relates to a method of preparing α-arylalkanoic esters. In accordance with this method, the α-arylalkanoic esters are prepared by reacting a trivalent iodine compound with a carbonyl compound in the presence of an orthocarboxylic ester and in a substantially anhydrous reaction mixture.

By the method of this invention, α-arylalkanoic esters represented by the general formula

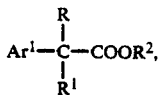

where $Ar^1$ is an aromatic hydrocarbon, R is a hydrogen atom or an alkyl group, $R^1$ is a hydrogen atom or an alkyl group, and $R^2$ is an alkyl group, are prepared by reacting a trivalent-iodine compound represented by the general formula:

wherein Ar is an aromatic hydrocarbon, and X and Y are each a group eliminated as an anion, with a carbonyl compound represented by the general formula:

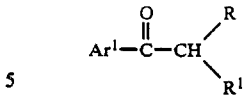

where $Ar^1$, R and $R^1$ are the same as defined above, in the presence of an orthocarboxylic ester represented by the general formula $ZC(OR^2)_3$, wherein $R^2$ is an alkyl group and Z is a hydrogen atom or an alkyl group, and in a substantially anhydrous reaction mixture.

In this reaction process Ar represents an aromatic hydrocarbon group, which may have one or more substituents on the aromatic ring. The substituent may be a linear or branched alkyl group such as methyl, ethyl, n- or iso-propyl, or n-, iso-, sec- or t-butyl group, an alkoxy group such as methoxy, ethoxy, n- or iso-propyloxy, or n-, iso-, sec- or t-butoxy group, an aryloxy group such as phenoxy, and acyloxy group such as acetoxy, n- or iso-propionyloxy, n-, iso-, sec- or t-butyloyloxy, or benzoyloxy group, or an electron attractive group such as a nitro, acetyl, propyl, benzoyl, nitrile or sulfonyl group.

$Ar^1$ also represents an aromatic hydrocarbon group which optionally may carry a substituent on the aromatic ring. The substituent may be a saturated hydrocarbon group such as an alkyl group having 1 to about 4 carbon atoms; an unsaturated aliphatic hydrocarbon group such as vinyl, ethynyl, or allyl group, an alkenyl or alkenyloxy group having such an unsaturated group; an alkoxy group such as methoxy, ethoxy, n- or iso-propyloxy, or n-, iso-, sec-, or t-butyloxy; an alkylthio group such as methylthio, ethylthio, n- or iso-propylthio, or n-, sec-, iso- or t-butylthio group; an arylthio group such as phenylthio; an aryl group, such as phenyl; a halogen atom or an amino group which is mono- or di-substituted by n- or iso-propyl, or n-, iso-, sec- or t-butyl group.

The groups R and $R^1$ may each independently represent an alkyl group, such as methyl, ethyl or propyl, or a hydrogen atom.

Preferably, the carbonyl compound is an acetophenone or propiophenone, the phenyl group of which optionally is substituted with an alkyl group, halogen or alkoxy group. The ratio of trivalent iodine compound to carbonyl compound desirably is at least 1:1. A preferred ratio is about 1:1.

In trivalent-iodine compounds

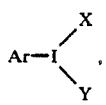

X and Y are groups which can be eliminated as an anion and include, for example, acyloxy groups such as acetoxy, trifluoroacetoxy, benzoyloxy, chloro and fluoro. X and Y may be the same group or different groups and may include a combination of an acyloxy group as X and a hydroxy group as Y.

The trivalent-iodine compounds can be produced in accordance with procedures well known in the art. For example, if X and Y are chlorine atoms,

can be prepared by reacting an iodinated aromatic hydrocarbon, Ar-I, with chlorine. If the dichloro trivalent-iodine compound obtained is allowed to react with acetic acid, the chlorine can be replaced with an acetoxy group. In the same way other trivalent-iodine compounds having other electronegative groups also can be produced.

The reaction is carried out in the presence of an orthocarboxylic ester represented by the general formula $CZ(OR^2)_3$. In this formula Z is a hydrogen atom or an alkyl group and $R^2$ is an alkyl group. Preferably, the compound is the methyl, ethyl or propyl ester of orthoformic acid. Ethyl orthoformate is especially preferred in comparison to other orthocarboxylic esters in that it is the most economical.

To obtain the desired α-arylalkanoic esters, the trivalent iodine compound and carbonyl compound are reacted together in the presence of the orthocarboxylic ester and sulfuric acid and in the presence or absence of an inert solvent. As used herein, "inert solvent" means a solvent which does not react with one or more of the trivalent iodine compound, the carbonyl compound and the orthocarboxylic ester or otherwise interfere with the reaction and in which each of the foregoing compounds is dispersible, with at least one of such compounds preferably being soluble in the solvent.

The ester-forming reaction is preferably conducted in the presence of sulfuric acid, preferably in an amount from about 0.2 to about 0.8 mole per mole of the carbonyl compound or ketone. Although the ester-forming reaction can be carried out using higher amounts of sulfuric acid (e.g. 1 mole or more per mole of ketone), the amount of orthocarboxylic acid needed is significantly decreased in comparison to the amount required when the reaction is conducted using sulfuric acid in amounts outside the above range. In Example 1 of Japanese Laid Open Patent Publication No. 163,345, wherein the molar ratio of sulfuric acid to the carbonyl compound is 1:1, the molar ratio of orthocarboxylic ester to carbonyl compound is about 14:1. In accordance with the method of this invention, the molar ratio of orthocarboxylic ester to carbonyl compound can be as low as about 0.6:1. If desired, additional orthocarboxylic ester, sufficient to bring the amount to about three or more moles per mole of carbonyl compound, can be employed. Typically, no more than 6-8 moles of orthocarboxylic ester per mole of carbonyl compound are needed to obtain high yields of product.

The above preferred range for the amount of sulfuric acid is critical to obtain good yields of arylalkanoic esters at low molar ratios of orthocarboxylic ester to ketone. At given low molar ratios of orthocarboxylic esters to ketone (OCE:K), use of molar ratios of sulfuric acid to ketone above about 0.8:1 and below about 0.2:1 result in substantially lower yields of arylalkanoic esters than are obtainable at acid:ketone ratios from about 0.2:1 to about 0.8:1 for the same OCE:K molar ratio.

Where, as preferred, the reaction is carried out neat (i.e., in the absence of an inert solvent), the molar ratio of sulfuric acid to ketone is preferably from about 0.2:1 to about 0.5:1.

Where the reaction is conducted in the presence of an inert solvent (e.g. methylene chloride, toluene, and acetic acid), the molar ratio of sulfuric acid to ketone is preferably from about 0.2:1 to about 0.7:1, and more preferably is about 0.5:1.

The reaction is preferably carried out under substantially anhydrous conditions (e.g. not more than 0.5% by weight water in the reaction mixture based on the weight of carbonyl compound), thereby increasing the obtainable yield of the arylalkanoic ester.

The reaction may be carried out at any suitable temperature, including for example minus 5° C. or less to 80° C. or more. Preferably, the reaction is conducted at low temperature (e.g., from about minus 5° C. to about 30° C. and more preferably from 0° C. to about 20° C.). At low OCE:K molar ratios (e.g. 2.0:1 or less), low reaction temperature results in higher yield of the arylalkanoic ester than is obtainable at higher temperature (e.g. 5 to 10% higher yield). Advantageously, the reaction may be conducted with good results at room temperature (about 20°-25° C.).

Suitable solvents for use as the inert solvent optionally employed in carrying out the reaction include hydrocarbons, halogenated hydrocarbons, lower aliphatic esters, lower aliphatic ethers, lower aliphatic nitriles, lower aliphatic alcohols, lower aliphatic acids and nitroparaffin. "Lower" is defined herein to include compounds having about 5 or fewer carbon atoms.

Examples of the solvents include linear or cyclic hydrocarbons having about 5 to about 7 carbon atoms, such as n-hexane, cyclopentane, cyclohexane, benzene and toluene; linear or cyclic halogenated hydrocarbons having 1 to about 6 carbon atoms, such as chloroform, dichloromethane and chlorobenzene; lower alkylesters such as methyl, ethyl and propyl esters of a fatty acid having 1 to about 3 carbon atoms, such as formic acid, acetic acid and propionic acid; lower aliphatic ethers having about 2 to about 4 carbon atoms such as dimethyl ether, diethyl ether and methyl ethyl ether; lower aliphatic nitriles, such as acetonitrile and propionitrile; lower aliphatic alcohols having 1 to about 4 carbon atoms, including methanol, ethanol, n- or isopropanol, and t-butanol; lower fatty acids having 1 to about 3 carbon atoms, i.e., formic acid, acetic acid and propionic acid; and nitroparaffin having 1 to about 2 carbon atoms, such as nitromethane and nitroethane. Preferred solvents are toluene, acetic acid and dichloromethane (most preferred).

The solvents may be used singly or as a mixture of two or more. If solvent recovery is taken into consideration, use of a single solvent may be preferable for ease of recovery of the reaction product.

Illustrative of unsuitable solvents are lower aliphatic ketones such as acetone, amides of a lower fatty acid di-substituted with lower alkyl groups such as dimethyl formamide, and lower dialkyl sulfoxides such as dimethyl sulfoxide. Such solvents interfere with the reaction of the present invention which will not proceed substantially in their presence.

Reaction time is dependent upon the carbonyl compound chosen as a reactant. The completion of the reaction can be determined by thin layer chromatography (TLC) by measuring for the disappearance of carbonyl compound. The α-arylalkanoic ester produced by the reaction can be recovered from the reaction mixture in accordance with conventional methods.

In preferred embodiments, the reaction is carried out neat to prepare ibuprofen methyl ester using per mole of p-isobutylpropiophenone as the carbonyl compound, iodobenzene diacetate (1 mole) as the trivalent iodine compound, methyl orthoformate (0.9 mole or less) as the orthocarboxylic ester, about 0.2 to 0.5 mole of concentrated sulfuric acid, substantially anhydrous reaction conditions (i.e., not more than 0.5% water in the reaction mixture based on the weight of the diacetate), a reaction temperature from 0° C. to about 20° C. and a reaction time sufficient to obtain ibuprofen methyl ester in good yield (e.g. 70% or more).

The substantially anhydrous reaction mixture in which the ester-forming reaction is carried out can be prepared using a trivalent iodine compound provided as a substance comprising water in amounts, e.g. from 3% or less to 10% or more. The water-containing iodine compounds, e.g. iodobenzene diacetate, are chemically dried by contacting a carboxylic anhydride with the substance in the presence of the carbonyl compound. Contacting is effected under conditions effective for converting at least a sufficient portion of the water to the acid corresponding to the anhydride to provide at least a portion of the reaction mixture. Preferably, such contacting is effected in the additional presence of sulfuric acid in a catalytically effective amount.

Suitable carboxylic anhydrides include, for example, acetic, propionic, butanoic, succinic and phthalic anhydride. Acetic anhydride is preferred. The anhydride may be employed in any effective amount. Preferably the amount of anhydride is sufficient to effect reaction of a sufficient portion of the water with the anhydride (e.g. acetic anhydride) to form the corresponding acid (e.g. acetic acid) such that the resulting chemically dried iodine compound can be employed in the ester-forming reaction mixture without detracting from its substantially anhydrous quality. It is further preferred that the amount of anhydride not be so high as to result in appreciable reduction in the yield of the arylalkanoic ester obtainable where the molar ratio of anhydride to water is 1:1. As shown by the examples, use of excess anhydride results in such reduction. In general, where it is desired to obtain yields of the arylalkanoic ester of about 50% of more, it is critical that the anhydride not be used in an excess corresponding to a molar ratio of excess anhydride to ketone of more than 0.5:1, preferably not more than 0.2:1 and more preferably not more than 0.1:1. The drying step is performed at any suitable temperature which may be, e.g. from about 0° C. to about 50 ° C. or less. Acids such as sulfuric acid catalyze the chemical drying reaction. In the absence of an acid catalyst, the drying step may require up to about 15 hours or more. Use of an acid catalyst, e.g. concentrated sulfuric acid, in an amount of about 3 m:mole per mole of anhydride reduces the required time to about 3 hours at temperatures as low as 10° C.

The present invention is further illustrated by the following examples, which are provided for illustrative purposes only and are not to be construed as limiting. All parts, percents and other amounts throughout this disclosure are by weight unless otherwise indicated.

EXAMPLE 1

Oven-dried iodobenzene diacetate (86.4 grams(g), 0.25 mol), which experience has shown is essentially free of water, was added with stirring to p-isobutylpropiophenone (47.5 g, 0.25 mol) at room temperature (about 22°-25° C.), which temperature was maintained throughout the procedure of this example unless indicated otherwise. To the resulting mixture was added water (approximately 15.8 g, 0.88 mol) with stirring to provide a mixture containing a known amount of water. To the resulting aqueous mixture were added sequentially, with stirring, acetic anhydride (75 ml, 0.88 mol) and, dropwise, concentrated sulfuric acid (about 96% $H_2SO_4$, 0.14 ml, 3 mmol). The resulting mixture was stirred 2 hours to ensure substantially complete reaction of the anhydride with the water and then cooled to 0° C. Trimethylorthoformate (24.6 ml, 0.225 mol) was then added with stirring, followed by dropwise addition, with stirring, of concentrated sulfuric acid (about 96% $H_2SO_4$, 2.5 ml, 0.05 mol) over 30 minutes. The ensuing reaction mixture was stirred an additional 2 hours at 0° C. to 20° C. The resulting ibuprofen-methyl-ester-forming reaction was quenched by adding 50 ml deionized water. HPLC (high performance liquid chromatography) analysis of the resulting reaction product comparing to an external standard, demonstrated 75% yield of ibuprofen methylester. The mixture obtained can be separated into an aqueous phase and an organic phase, followed by isolation of purified ibuprofen methyl ester from the organic phase by column chromatography or distillation. Alternatively, the crude ester can be hydrolyzed by treating with 50% aqueous sodium hydroxide, followed by extraction of the resulting aqueous phase with heptane. Acidification of the aqueous phase and recrystallation of the solid precipitate yields high-purity ibuprofen.

EXAMPLE 2

The procedure of Example 1 was followed except that (a) in lieu of the oven-dried iodobenzene diacetate and water addition, there was employed a total of 86.4 g of a crude diacetate product containing 93.2% iodobenzene diacetate (0.25 mol-pure basis) and 4.3% water (3.7 g, 0.21 mol), the product having a total loss on drying of 6.8% (including the water), and (b) the amount of acetic anhydride was 18 ml (0.21 mol), resulting in 74% yield of ibuprofen methyl ester.

EXAMPLES 3-6

The procedure of Example 2, in which the molar ratio of acetic anhydride to water was 1:1 (as in Example 1), was followed except that the amount of acetic anhydride (AA) was increased above such molar ratio to provide excess AA in amounts corresponding to the excess AA:ketone molar ratios shown in the table below. The resulting yield of ibuprofen methyl ester is also shown in the table.

| Ex. | AA:Ketone Molar Ratio | Yield |
| --- | --- | --- |
| 3 | 0.2:1 | 63% |
| 4 | 0.5:1 | 47% |
| 5 | 1.0:1 | ·19% |
| 6 | 2.0:1 | 6% |

Although the foregoing description has been given in terms of sulfuric acid, it is to be understood that good results may also be obtained with other acids such as aryl sulfonic acids (e.g., p-toluene sulfonic acid), alkyl sulfonic acids (e.g., methane sulfonic acid), perchloric acid and nitric acid (preferably of high concentration and, more preferably, fuming nitric acid). In general, all or part of the sulfuric acid in the above description may be replaced with one or more of the other acids, each at one gram-equivalent per one gram-equivalent of replaced sulfuric acid.

BEST MODE CONTEMPLATED

The best mode contemplated for carrying out this invention has been set forth in the above description, for example, by way of setting forth preferred materials and operating conditions, including but not limited to preferred ranges and values of amounts and other non-obvious variables material to successfully practicing the invention in the best way contemplated at the time of executing this patent application.

It is understood that the foregoing detailed description is given merely by way of illustration and that many modifications may be made therein without departing from the spirit or scope of the present invention.

What is claimed is:

1. A method for preparing an α-arylalkanoic ester represented by the general formula

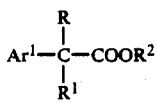

wherein $Ar^1$ is an aromatic hydrocarbon, R is an alkyl group or a hydrogen atom, $R^1$ is an alkyl group or a hydrogen atom, and $R^2$ is an alkyl group, which comprises reacting, under α-arylalkanoic ester-producing conditions, a trivalent iodine compound represented by the general formula

wherein Ar is an aromatic hydrocarbon and X and Y each represents a group which can be elimiated as an anion, with a carbonyl compound represented by the general formula

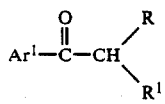

wherein $Ar^1$, R and $R^1$ are as defined above, in the presence of an orthocarboxylic ester represented by the general formula

$ZC(OR^2)_3$ wherein Z is an alkyl group or a hydrogen atom and $R^2$ is as defined above, via an improved method wherein the reaction between iodine and carbonyl compounds is effected in a substantially anhydrous mixture.

2. The method of claim 1 wherein at least a portion of said mixture is prepared by a process wherein said trivalent iodine compound is provided as a substance comprising water, which comprises contacting a carboxylic anyhydride with said substance in the presense of said carbonyl compound under conditions effective for converting at least a sufficient portion of the water to the acid corresponding to said anhydride.

3. The method of claim 2 wherein the contacting step is effected in the additional presence of sulfuric acid a catalytically effective amount.

4. The method of claim 2 wherein said anhydride is selected from the group consisting of acetic, propionic, butanoic, succinic and phthalic anhydride.

5. The method of claim 2 wherein said substance comprises up to 10% water.

6. The method of claim 2 wherein said anhydride is not employed in an excess over a molar ratio of the anhydride to the water corresponding to a second molar ratio of excess anhydride to said carbonyl compound of more than 0.5:1.

7. The method of claim 6 wherein said second molar ratio is not more than 0.2:1.

8. The method of claim 7 wherein said molar ratio of anhydride to water is about 1:1.

9. The method of claim 1 wherein the reaction is conducted in the absence of an inert solvent.

10. The method of claim 9 wherein the amount of sulfuric acid is from about 0.2 to about 0.5 mole per mole of said carbonyl compound.

11. The method of claim 1 wherein the reaction is conducted in the presence of an inert solvent.

12. The method of claim 1 wherein said solvent is selected from the group consisting of hydrocarbons, halogenated hydrocarbons, lower aliphatic esters, lower aliphatic ethers, lower aliphatic alcohols, lower aliphatic nitriles, lower aliphatic acids, nitroparaffin and compatible mixtures thereof.

13. The method of claim 12 wherein said solvent is selected from the group consisting of a linear or cyclic hydrocarbon comprising 5 to about 7 carbon atoms; a linear or cyclic halogenated hydrocarbon comprising 1 to about 6 carbon atoms; methyl, ethyl, n- or isopropyl ester of a fatty acid comprising 1 to about 3 carbon atoms; an aliphatic ether comprising about 2 to about 4 carbon atoms; an alkyl cyanide comprising 1 to about 2 carbon atoms; an aliphatic alcohol comprising 1 to about 4 carbon atoms; a fatty acid comprising 1 to about 3 carbon atoms and nitrated paraffin comprising 1 to about 2 carbon atoms.

14. The method of claim 13 wherein said solvent is selected from the group consisting of methylene chloride, toluene and acetic acid.

15. The method of claim 14 wherein said solvent is methylene chloride and the amount of sulfuric acid is from about 0.2 to about 0.7 mole per mole of said carbonyl compound.

16. The method of claim 15 wherein said amount is about 0.5 mole.

17. The method of claim 1 wherein Ar is a phenyl group which is optionally substituted by an alkyl, alkoxy, aryloxy, acyloxy or electron attractive group; X and Y are each a halogen atom or an aliphatic or aromatic acyloxy group; $Ar^1$ is a phenyl group which is optionally substituted by a saturated or unsaturated hydrocarbon, aryl, alkoxy, alkenyloxy, alkynyloxy, alkythio, substituted amino group or a halogen atom; and R and $R^1$ are each a hydrogen atom or an alkyl group comprising one to three carbon atoms.

18. A method as claimed in claim 1 where Ar is a phenyl group which optionally carries a substituent comprising an alkyl group having 1 to about 4 carbon atoms, an alkoxy group comprising 1 to about 4 carbon atoms, a phenyloxy group, an acyloxy group comprising 1 to about 4 carbon atoms, or a nitro, acyl, cyano, or sulfonyl group; X and Y each comprise a halogen atom or an aliphatic acyloxy group comprising about three or fewer carbon atoms; $Ar^1$ is a phenyl group which optionally carries a substituent comprising an alkyl group comprising 1 to about 4 carbon atoms, a phenyl group, an alkoxy group comprising 1 to 4 carbon atoms, a phenoxy group, an aliphatic acyloxy group, benzoyloxy group, alkylthio group comprising 1 to about 4 carbon atoms, or mono- or di-substituted alkyl or phenyl amino group or a halogen atom; and R and $R^1$ each comprises a hydrogen atom or an alkyl group comprising 1 to 3 carbon atoms.

19. The method of claim 1 wherein said orthocarboxylic ester comprises methyl orthoformate, ethyl orthoformate, or propyl orthoformate.

20. The method of claim 1 wherein the molar ratio of said orthocarboxylic ester to said carbonyl compound is about 0.6:1 to about 8:1.

21. The method of claim 1 wherein the ratio of trivalent iodine compound to carbonyl compound is about 1:1 and the reaction is conducted at room temperature.

22. The method of claim 1 wherein the sulfuric acid is concentrated sulfuric acid.

23. The method of claim 1 wherein said carbonyl compound is p-isobutylpropiophenone, said iodobenzene compound is iodobenzene diacetate and said arylalkanoic ester is an ester of ibuprofen.

24. The method of claim 23 wherein said orthocarboxylic acid ester is methyl orthoformate and the ibuprofen ester is the methyl ester.

25. The method of claim 24 wherein said reaction is conducted under substantially anhydrous conditions in the absence of an inert solvent, the sulfuric acid is concentrated sulfuric acid and the amount of sulfuric acid is from about 0.2 to about 0.5 mole per mole of said carbonyl compound and the mole ratio of methyl orthoformate to said carbonyl compound is less than 1:1.

* * * * *